United States Patent [19]
Horrobin et al.

[11] Patent Number: 5,466,841
[45] Date of Patent: Nov. 14, 1995

[54] FORMULATIONS CONTAINING UNSATURATED FATTY ACIDS

[75] Inventors: David F. Horrobin, Guildford; Austin McMordie; Mehar S. Manku, both of Carlisle, all of England

[73] Assignee: Scotia Holdings PLC, Surrey, England

[21] Appl. No.: 187,042

[22] Filed: Jan. 27, 1994

[30] Foreign Application Priority Data

Jan. 27, 1993 [GB] United Kingdom .................... 9301629

[51] Int. Cl.[6] ...................................... C07F 9/02
[52] U.S. Cl. ................................. 554/79; 554/80
[58] Field of Search ............................ 554/79, 80; 514/74

[56] References Cited

U.S. PATENT DOCUMENTS

| | | | |
|---|---|---|---|
| 3,577,446 | 5/1971 | Rakhit | 260/403 |
| 5,260,464 | 11/1993 | Della Valle et al. | 554/80 |

FOREIGN PATENT DOCUMENTS

| | | |
|---|---|---|
| 0147741 | 7/1985 | European Pat. Off. . |
| 0296751 | 12/1988 | European Pat. Off. . |
| 3347269 | 7/1985 | Germany . |
| WO89/03836 | 5/1989 | WIPO . |

OTHER PUBLICATIONS

Chemical Abstracts, vol. 101, No. 3, Jul. 1984 Schmitz et al Abstract No. 023203 "1–trans–Parinaroyl phospholipids . . . ".

Biochemistry 1982, 21, 5685–5689 Welti et al "Partition of Parinaroyl Phospholipid Probes . . . ".

Biochimica et Biophysica Acta, 713 (1982) 73–79, Mahadevappa et al "The Molecular Species Composition of . . . ".

Biochimica et Biophysica Acta, 1123, (1992) 41–50 Menguy et al "Apparent relative retention of the phosphatidylethanolamine . . . ".

J. Neurochemistry, vol. 55, 1990, 1–4, pp. 1200–1207 Lin et al "Effects of Dietary n-3 Fatty Acids . . . ".

Biochem. Cell Biol., 88, vol. 66 pp. 1163–1168 Ishinaga et al "Composition of Phospholipid moelcular . . . ".

Biochimica et Biophysica Acta, 450 (1976) 210–224 Fallani et al "Structural Analysis of Phosphatidyl . . . ".

Chemical Abstracts, vol. 107, No. 23, Dec. 1987 No. 218003 Noguchi et al "Polymerizable glycerophospholipids".

Chemical Abstracts, vol. 116, No. 6, Feb. 1992, No. 046304 Hibino et al "Infusion solutions containing stable . . . ".

Chemical Abstracts, vol. 111, 1989, No. 17, No. 154301 Hibino et al "Preparation of phosphatidylcholines . . . ".

Chemical Abstracts, vol. 112, No. 23, Jun. 1990, No. 217461 Hibino et al "Preparation of phosphatidylcholines . . . ".

*Primary Examiner*—José G. Dees
*Assistant Examiner*—Deborah D. Carr
*Attorney, Agent, or Firm*—Nixon & Vanderhye

[57] ABSTRACT

A phospholipid comprising two different unsaturated fatty acids, the fatty acids being selected from the twelve n-6 and n-3 essential fatty acids, oleic acid, parinaric acid and combinic acid.

16 Claims, No Drawings

FORMULATIONS CONTAINING UNSATURATED FATTY ACIDS

This invention relates to phospholipids composed of two different unsaturated fatty acids.

BACKGROUND OF THE INVENTION

Unsaturated fatty acids, particularly the essential fatty acids (EFAs), shown in Table I below and certain others, have a range of possible medical uses.

Besides the essential fatty acids, there are more particularly oleic acid, parinaric acid and other fatty acids with conjugated double bonds, and columbinic acid, a fatty acid with non-conjugated bonds which, while not being an essential fatty acid, can correct many of the features of essential fatty acid deficiency. Parinaric acid is an 18:4 n-3 acid (9 cis, 11 trans, 13 trans, 15 cis); columbinic acid is an 18:3 n-6 acid (6, 9 cis, 13 trans).

The bodily conversions of the main series of EFAs appear in the table, which is:

TABLE 1

| n-6 | n-3 |
|---|---|
| 18:2 delta-9, 12 (linoleic acid) | 18:3 delta-9, 12, 15 (alpha-linolenic acid) |

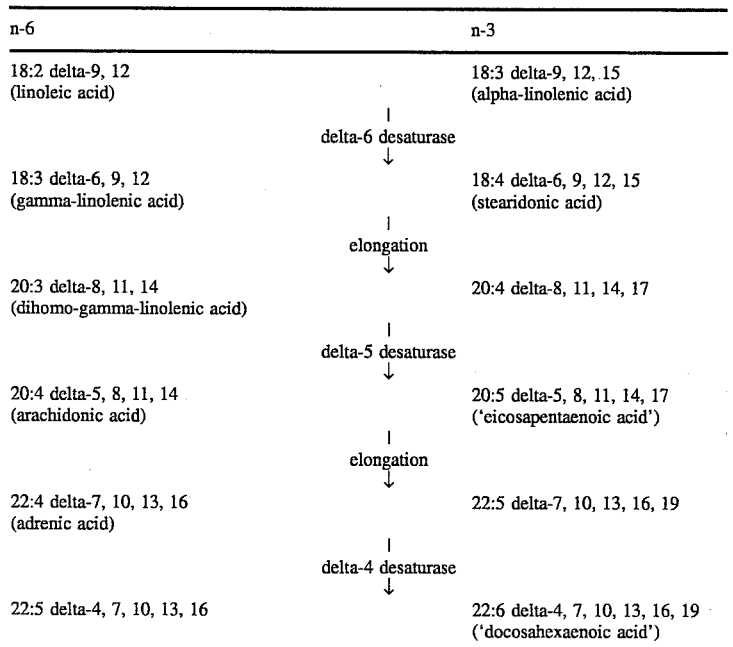

| n-6 | n-3 |
|---|---|
| 18:3 delta-6, 9, 12 (gamma-linolenic acid) | 18:4 delta-6, 9, 12, 15 (stearidonic acid) |
| 20:3 delta-8, 11, 14 (dihomo-gamma-linolenic acid) | 20:4 delta-8, 11, 14, 17 |
| 20:4 delta-5, 8, 11, 14 (arachidonic acid) | 20:5 delta-5, 8, 11, 14, 17 ('eicosapentaenoic acid') |
| 22:4 delta-7, 10, 13, 16 (adrenic acid) | 22:5 delta-7, 10, 13, 16, 19 |
| 22:5 delta-4, 7, 10, 13, 16 | 22:6 delta-4, 7, 10, 13, 16, 19 ('docosahexaenoic acid') |

The above pathways are not normally reversible nor, in man, are n-3 and n-6 series acids inter-convertible.

The acids, which in nature are of the all-cis configuration, are systematically named as derivatives of the corresponding octadecanoic, eicosanoic or docosanoic acids, e.g. delta-9, 12 octadecadienoic acid or delta-4, 7, 10, 13, 16, 19-docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexaenoic acid as such are also used.

The alpha isomer of linolenic acid was characterised earlier than gamma-linolenic acid and reference in the literature simply to linolenic acid, especially in the earlier literature, is to the alpha-acid.

Many of these fatty acids have actions which appear synergistic with one another. For example, gamma-linolenic acid (GLA) exerts one set of anti-inflammatory effects while eicosapentaenoic acid (EPA) exerts another set of anti-inflammatory effects. Many of the fatty acids are easily oxidised, while oleic acid exerts potent anti-oxidant effects. Arachidonic acid (AA) is an important constituent of cell membranes but can be harmful if converted to pro-inflammatory, pro-thrombotic and vasoconstrictor metabolites, such as thromboxne $A_2$ or leukotrienes: it is therefore useful to administer AA with a fatty acid which reduces its conversion to the harmful metabolites.

In most countries further, the guidelines for pharmaceutical products militate against ready acceptance of drugs which are mixtures of compounds, such as mixtures of fatty acids. It is therefore preferable to seek approval for single molecules.

It would therefore be desirable to have a vehicle, for administration of fatty acids, incorporating different fatty acids in the form of a single molecule, and we propose the use of phospholipids such as P-serine, P-choline, P-ethanolamine, or P-inositol (P-phosphotidyl), which have two sites at which fatty acids may be incorporated. Such phospholipids are close to the natural phospholipids and are therefore appropriate single molecules for delivery of two different fatty acids.

DESCRIPTION OF THE INVENTION

The invention thus makes use of phospholipids in which one site is occupied by one fatty acid and the other is occupied by a different fatty acid, particularly one which has an action additive to or synergistic with the first. The fatty acids may be prepared by chemical synthesis, or by extraction and purification from natural products, in each case by methods known in themselves, and may be incorporated into phospholipids by methods known in themselves.

The fatty acids to be used for preparation of the phospholipids are the twelve essential fatty acids shown in table 1, oleic acid, columbinic acid and parinaric acid.

Preferably there are present fatty acids selected from GLA, DGLA, AA, EPA and DHA.

Among fatty acids of particular interest are gamma-linolenic acid (GLA), dihomo-gamma-linolenic acid (DGLA), arachidonic acid (AA), eicosapentaenoic acid (EPA) and docosahexaenoic acid (DHA). Of particular interest therefore are phospholipids containing any of these particular fatty acids at both positions on the phospholipid, especially phospholipids containing the following pairs of fatty acids:

Gamma-linolenic acid (GLA) or dihomo-gamma-linolenic acid (DGLA) with arachidonic acid (AA)
GLA or DGLA with eicosapentaenoic acid (EPA)
GLA or DGLA with docosahexaenoic acid (DHA)
AA with EPA
AA with DHA
EPA with DHA Because of the inevitable limitations of the methods of synthesis and separation of the phospholipids, any phospholipid preparation made for use in pharmaceutical products or foods is likely in practice to be a mixture of different phospholipids. This invention therefore for preference covers situations in which the specified phospholipids make up at least 20%, preferably more than 40%, very preferably more than 70% and ideally more than 90% of the total phospholipid present.

The phospholipids may for example be used in the preparation of foods or skin care preparations or of pharmaceutical agents for oral, enteral, parenteral (intravenous, subcutaneous, intramuscular or any other such route), topical, rectal, vaginal or other route of administration. They may be desirably administered in pharmaceutical forms at doses of 1 mg to 100 g, preferably 100 mg to 20 g and very preferably 500 mg to 4 g of the specified phospholipid per day. When used in foods or preparations for enteral, parenteral or topical administration they may desirably be made into formulations containing by weight 0.01% to 60%, preferably 0.1% to 30% and very preferably 1% to 20% phospholipid of the specified phospholipid.

Suitable pharmaceutical dosage forms are for example a hard or soft gelatin capsule, a tablet, a pastille, a cream, a lotion or emulsions. A food may for example be a whip, a foam, a powder or a chocolate. For cosmetic use creams and the like may be used.

Synthetic Routes to Phospholipids

Four classes of phospholipids are considered:
I. phospholipid acids (PA)
II. phosphatidylcholines (PC)
III. phosphatidylethanolamines (PE)
IV. phosphatidylserines (PS)
In all cases the target molecules are diacyl phospholipids.
Phospholipid synthesis can be divided into two approaches.

(i) phosphorylation first, then acylation
(ii) acylation first then phosphorylation Phospholipid syntheses are usually considered as either partial synthetic routes or total synthetic routes. Partial synthesis takes advantage of naturally occurring phospholipids as starting materials while total synthesis usually starts with a glycerol derivative. For mixed acid phospholipid synthesis the second approach is generally more feasible.

(I) Phosphatidic Acid Synthesis (i) Phosphorylation Step First

Method (a)

Glycerophosphatidic acid has been acylated with fatty acid anhydride in 60–80% yields. This route is suited to the synthesis of PA's with the same acyl group in both positions but may be adapted to mixed acid synthesis as for example at II (i)(a). Salts of the fatty acid in question are often added, to reduce the degree of cyclic phosphate formation and phosphate migration.

Glycerolphosphatidic acid has been prepared on a large scale (300 g) by enzymatic phosphorylation of glycerol. The reaction, carried out in a fermenter, uses immobilised glycerol kinase, a catalytic amount of ATP and an enzymatic system for ATP regeneration. This is the most attractive route for the large scale production GPA.

Cyclic phosphate formation can be avoided if the phosphate group is in the form of a triester. GPA has been prepared by the reaction of sodium dihydrogen phosphate with glycidol and the following reaction may be used:

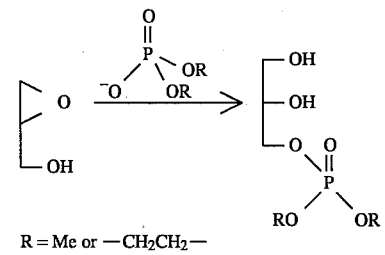

R = Me or —CH₂CH₂—

The intermediate phosphotriester is then acylated with an acid chloride and conversion to the PA completed by removal of the phosphate protecting groups, for example by trimethylsilyl iodide.

Method (b)

PA's have been prepared in quantitative yield on a small scale by hydrolysis of PC's using phospholipase D (from Streptomyces chromofuscus).

(ii) Acylation first

PA's have been prepared from the corresponding 1,2-diacylglycerol. This starting material is common to a number of the syntheses and method for its preparation are given below. The following are routes to the PA's using it.

Method (a)

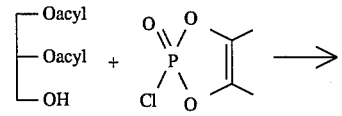

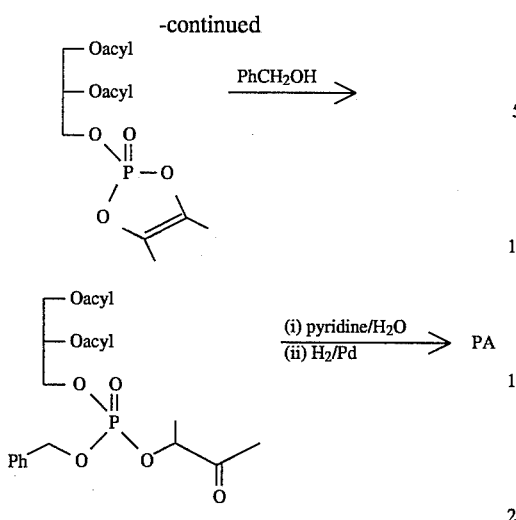

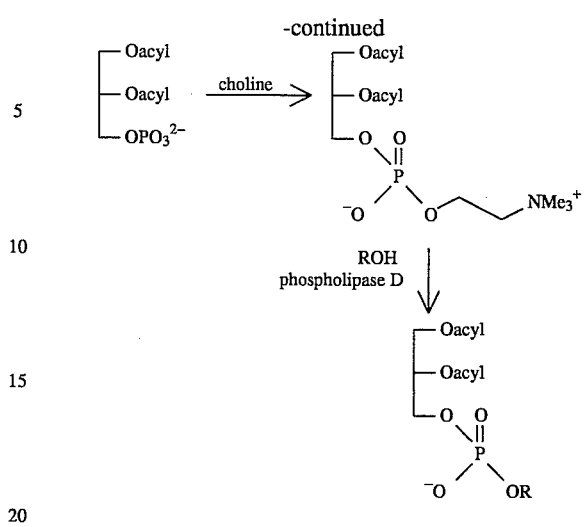

As given, this is suitable only for saturated acyl groups. However, choice of an alcohol other than benzyl alcohol expands the applicability of this route.

Method (b)

High yield (>90%) synthesis of PA is given by reaction of 1,2-diacylglycerol with $POCl_3/Et_3N$.

Method (c)

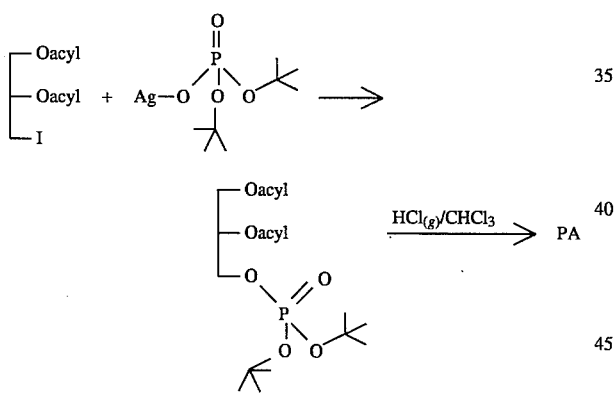

This route solves the problem of acyl group migration provided the expense, and interaction of silver ions with polyunsaturated fatty acids, is acceptable.

Method (d)

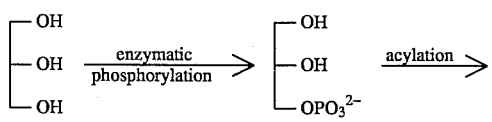

This gives same acid PA's, PC's and PS's as well as novel lipid phosphodiesters. The initial phosphorylation uses glycereol as a starting material and produces glycerol phosphate (GPA) in good yields and in optically pure form. The method starts with the purification of GPA as a crystalline 4-N,N-dimethylaminopyridine salt and continues with acylation using fatty acid anhydride and conversion of the PA to PC. The final step is phospholipase D mediated transphosphatidylation reaction.

Method (e)

This uses a mild phosphorylating agent which does not lead to acyl group migration:

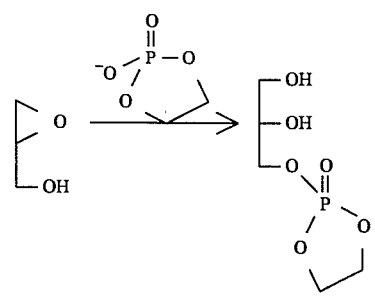

(II) Phosphatidylcholine Synthesis (i) Phosphorylation Step First

Method (a)

Glycerophosphatidyl choline has been acylated using a variety of procedures with yields ranging from 67 to 88%. The use of ultrasound reduces the reaction time. This route is limited to PC's with the same acyl group at C1 and C2. However, using any one of a number of phospholipase $A_2$ enzymes, followed by reacylation, mixed acid PC's can be prepared. Glycerophosphatidyl choline is commercially available and can also be readily prepared from egg yolk as a colourless crystalline cadmium chloride complex. A chemical synthesis is the opening of glycidol with a suitably protected phosphate.

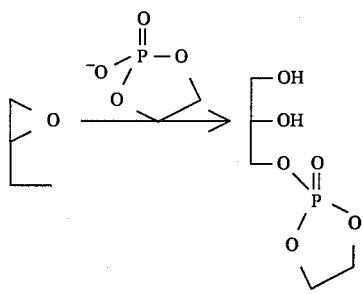

The phosphate diester is then acylated with fatty acid chloride and converted to PC by reaction with trimethylamine under anhydrous conditions. Alternatively, initial treatment with aqueous trimethylamine yields GPC which is then acylated as discussed above. This phosphotriester can also be easily prepared from solketal.

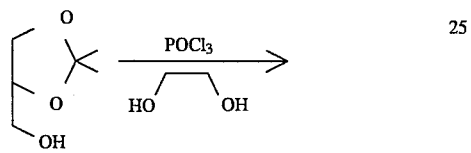

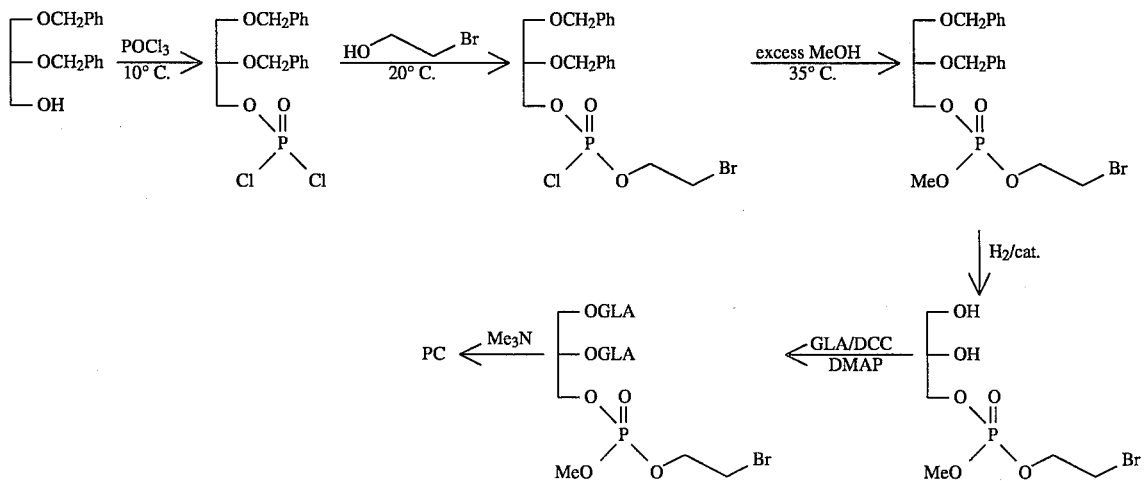

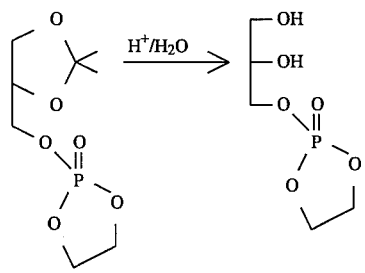

Alternatively, GPC can be prepared by reaction of solketal with phosphorus oxychloride followed by choline, with subsequent acid-catalysed removal of the acetonide group.

Method (b)

Synthesis of GPC or PC by the coupling of solketal or a 1,2-diacylglycereol and choline phosphate, the choline phosphate being prepared by enzymatic phosphorylation of choline.

Method (c)

Cyclic phosphate formation is avoided by keeping the phosphate as a phosphotriester until a late stage. For example GPC protected as a triester is produced as follows:

Method (d)

PC's are prepared by exhaustive methylation of phosphatidylethanolamines.

Method (e)

PCs are prepared by reaction between PA's and choline under the influence of a phosphate activating agent as in I (ii)(d) above. Trichloracetonitrile and 2,4,6-triisopropylbenzenesulfonyl chloride can both be used.

Method (f)

Mixed acid PC's can be prepared by phospholipase $A_2$, mediated reacylation of lysophosphatidylcholine with oleic acid in toluene. Other acid derivatives and other reaction conditions can be used. Lipozyme can be used to mediate the selective esterification of GPC at the 1-position by an acid anhydride in 71% yield. For example in a synthesis comprising sequential use of these two enzymes.

(ii) Acylation first

There is a wide range of reagents for the conversion of a 1,2-diacylglycerol into a PC.

Method (a)

The simplest route is the reaction with phosphorus oxychloride followed by choline (as a chloride, tosylate or tetraphenylborate salt). A modification of this route is the use of ethane-1,2-diol in the place of choline and although this adds more steps to the synthesis, purification of the intermediate (A) is easier than direct PC purification.

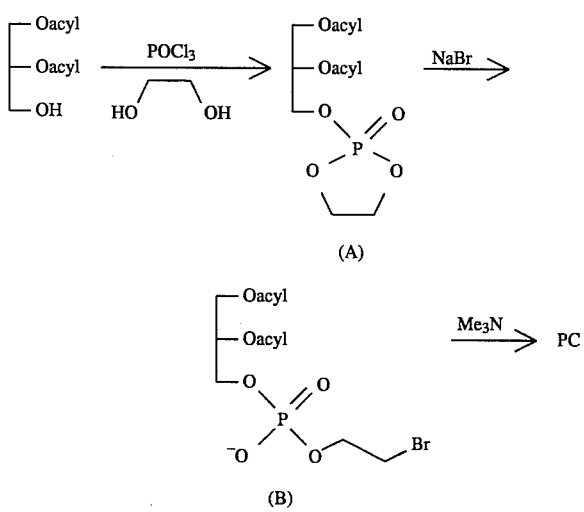

Compound (A) can also be converted to a PC by reaction with trimethylamine. Preparation of mixed acid PC's involves phospholipase A$_2$ hydrolysis of (B) followed by reacylation with a second fatty acid anhydride in the presence of perchloric acid and subsequent treatment with trimethylamine. The function of the perchloric acid is to minimise acyl group migration. Reacylation of lysophosphatidylcholine is however chemically difficult because the hydroxyl group is very sterically crowded, which can lead to problems of acyl or phosphate migration under the forcing conditions needed for reacylation.

Method (b)

Phosphorylation with a suitably protected phosphoryl chloride to yield either intermediate (A) or (B) above is followed by reaction with trimethylamine.

Method (c)

This is the route as in I (ii)(d) above (III) Phosphatidylethanolamine Synthesis (i) Phosphorylation Step First Method (a)

Glycerophosphatidylethanolamine is commercially available, and though the amino group is an active nucleophile, thus interfering with the acylation step it can be used as a starting point for PE synthesis.

Method (b)

PE's are prepared from PC's by phospholipase D catalysed transphosphitylation.

Method (c)

Using 2,4,6-triisopropylbenzenesulfonyl chloride as an activating agent a protected form of ethanolamine is coupled to a PA. The protecting group is subsequently removed.

Method (d)

Synthesis of mixed acid PE:

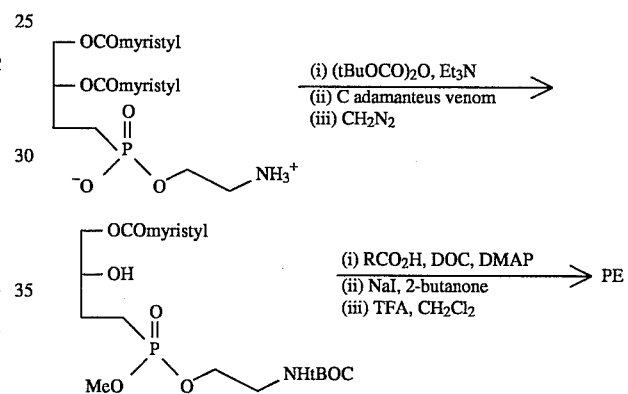

Protection of the phosphate as a methyl ester gives a good yield for acylation of the intermediate lysophosphatidylethanolamine.

Method (e)

A protected form of GPE is acylated. Starting from solketal, reaction with phosphorus oychloride followed by N-protected ethanolamine and finally acid catalysed deacetonisation of the adduct yields protected GPE as a phosphodiester. An improvement to synthesis of protected GPE phosphoetriester as shown below:

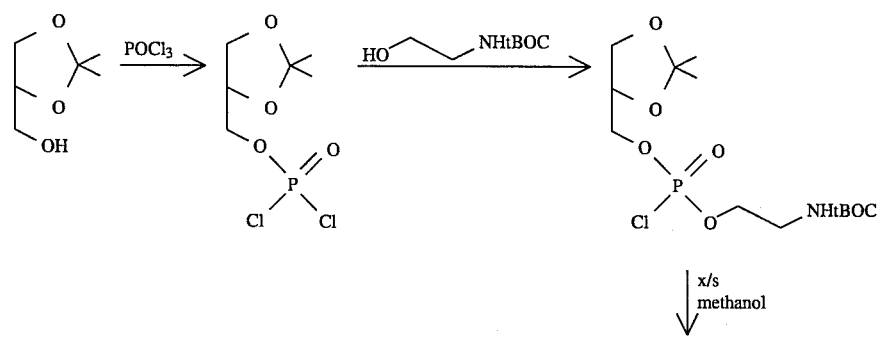

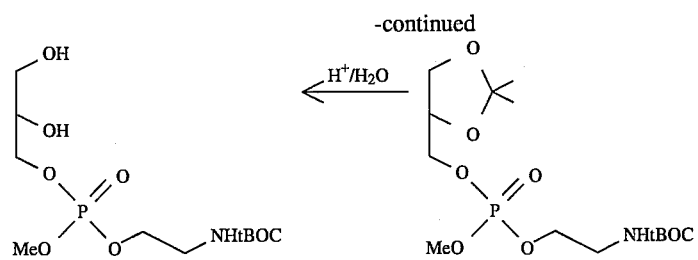

After acylation, removal of the methyl group is by using sodium iodid in butan-2-one.

Further, if N-tBOC ethanolamine is O-phosphorylated it can be coupled (using either trichloroacetonitrile, DCC or 2,4,6-triisopropylbenzensulfonyl chloride) with either a 1,2-diacylglycerol to yield a protected PE or with solketal to yield (after removal of the acetonide group) protected GPE.

(ii) Acylation first

Method (a)

PE's can be prepared from 1,2-diacylglycerols by sequential addition of POCl₃ and either ethanolamine or its N-tBOC derivative. When free ethanolamine is used an oxazaphosphalane is formed. This is opened under very mild conditions (aqueous acetic acid; room temperature; 2 h). The product PE precipitates from solution, thus making this method attractive for larger scale syntheses.

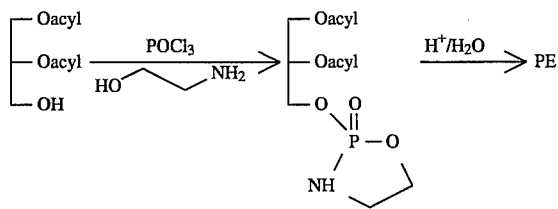

Method (b)

PE's have been prepared by reaction of glycerol iodohydrin diesters with a silver salt of a suitably protected ethanolaminephosphate. See PA synthesis method (c).

Method (c)

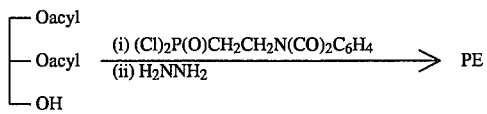

Method (d)

This is the route as in I (ii)(d) above.

(IV) Phosphatidylserine Synthesis (i) Phosphorylation Step First

Method (a)

Glycerophosphorylserine is commercially available. A protected form of GPS (N-phthaloyl derivative) has been prepared. After attachment of the acyl groups reaction with hydrazine yields PS.

Method (b)

PS has been prepared by enzyme-catalysed transphosphatidylation of PC in the presence of serine, phospholipase D (from Savoy cabbage leaves) in low yield. Using a Streptomyces phospholipase D preparation almost quantitative conversion is given.

Method (c)

Coupling of a PA and a protected serine derivative promoted by 2,4,6-triisopropylbenzenesulfonyl chloride yields PS's in 60–95% yields.

Method (d)

Glycerophosphatidylserine has been prepared from soiketal using phosphoramidite methodology

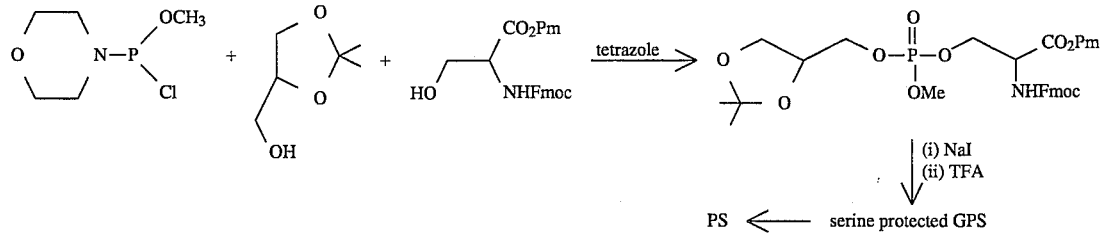

(ii) Acylation first

Method (a)

Starting from a 1,2-diacylglycerol reaction with POCl$_3$ followed by reaction of the intermediate phosphodichloridate with a protected serine derivative group is a good route to PS's. Using a serie derivative protected only on the carboxyl group an intermediate oxazaphospholane is formed which undergoes facile cleavage.

Method (b)

This is the route as in I (ii)(d) above.

Preparation of 1,2-diacylglycerols

A requirement of phospholipid chemistry (and triglyceride chemistry) is the preparation of pure same-acid and mixed-acid 1,2-diacylglycerols, particularly large scale preparation. A problem is that 1,2-diglycerides tend to isomerise very easily to 1,3-diglycerides, complicating purification of the final phospholipid. There is wide variety of protecting groups that can be used. For example, the trityl group has been successfully used for small scale preparation of 1,2-diacylglycerols. It is removed under extremely mild conditions (column chromatography on silicic/boric acids) with the undesired sideproduct, triphenylmethanol, eluting before the diacylglycerol. An alternative procedure for the removal of the trityl group is reaction with boron trifluoride etherate, though triphenylmethanol has to be removed from the reaction product.

A very satisfactory route uses the levulinoyl protecting group. The route is as shown on the next page. Very little acyl migration accompanis the deblocking procedure.

A second valuable protecting group is the tert-butyldimethylsilyl group. Removal of the silyl group using boron trifluoride-etherate is effected without problems of migration of the acyl group. The reaction is quenched with excess dry triethylamine, immediately adding the phosphorylating agent, thereby acoiding an aqueous work up.

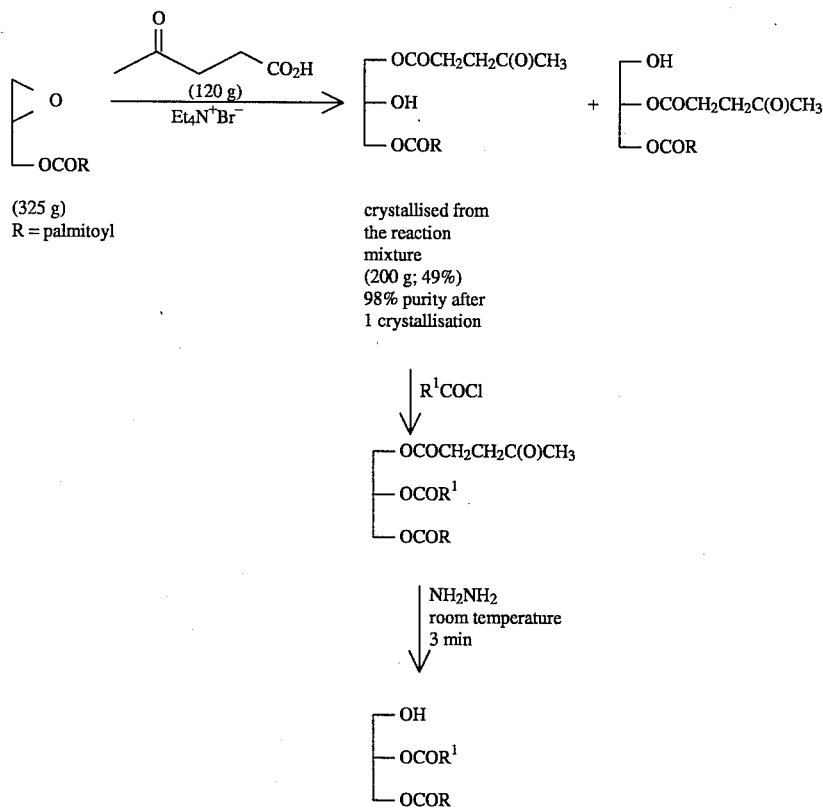

Aqueous work up on a large scale allows time for acyl migration to occur. This particular silyl group is bulky enough to react with a 1-monoacylglycerol exclusively at the 3 position, whereas use of the trimethylsilyl group leads to a mixture of silyethers at the 2 and 3 positions. The synthesis takes the following course:

(i) reaction of RCO$_2$H with glycidol to yield 1-monoacylglycerol (ii) reaction of the 1-monoacylglycerol with TBDMS-Cl to yield the 1-acyl-3-silyl glycerol (iii) reaction of this with R'COCl to yield 1-acyl-2-acyl'-3-silyl glycerol (iv) removal of the silyl group with BF$_3$Et$_2$O (v) quenching of excess boron trifluoride with excess triethylamine and reaction with the phosphorylating reagent of choice

SYNTHESIS OF MIXED ACID PHOSPHATIDYLCHOLINES

Approach 1

Regioselective hydrolysis of a same-acid diacylphosphatidylcholine with a phospholipase A$_2$ enzyme followed by reacylation with a different acid.

Approach 2

Phoshorylation of a pre-pared 1,2-diacylglycerol. There is a wide range of methods for the small scale production of 1,2-diacylglycerols. Care needs to be taken to avoid formation of the 1,3-isomer as this complicates the purification of the final phosphatidylcholine.

Approach 3

The following:

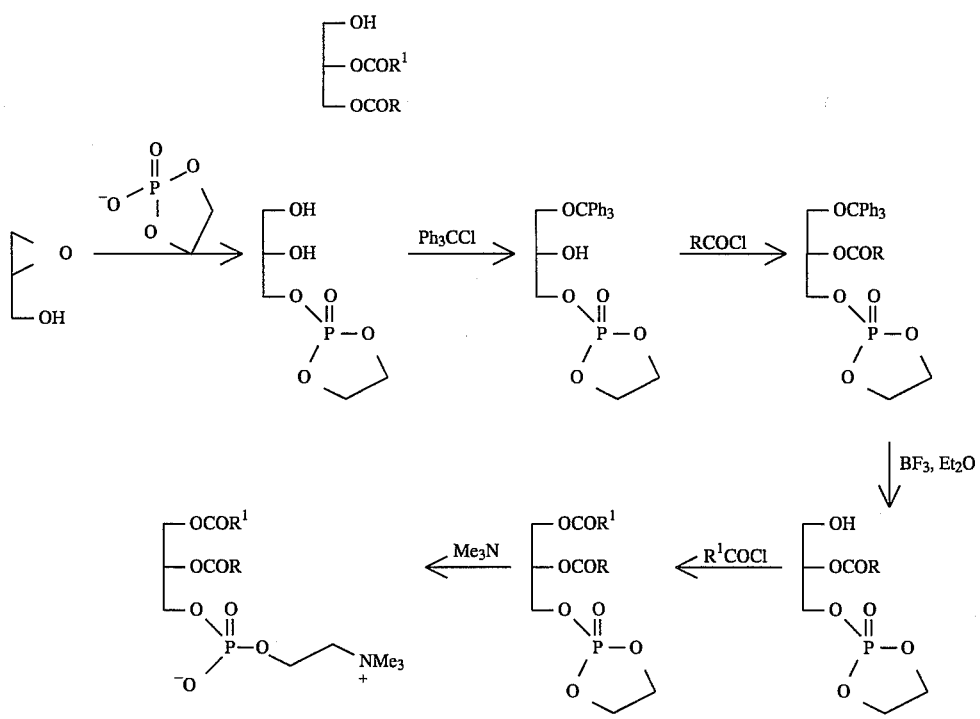

Approach 4

Lipase mediated monoacylation (exclusively in the 1 position) of GPC has been reported using a vinyl ester of the desired fatty acid. The other product of this reaction is acetaldehyde which quickly evaporates out of the reaction mix. This means that under suitable conditions the lipase reaction is effectively irreversible.

Approach 5

Preparation of triglycerides by lipase catalysed exchange of the 1,3-acyl groups of a same-acid trigiyceride with an excess of a fatty acid ester. This approach can be used to prepare a mixed acid phosphatidylcholine by starting with a same-acid PC and an excess of a simple ester of the desired fatty acid.

Synthesis of 1-(z-z-z-6,9,12-octadecatrienoyl)-2-(z-9-octadecenoyl)-rac-glycero-3-phosphocholine (i) A mixture of solketal (3.3 g, 25 mmol), tetrabutylammonium hydrogen sulfate (425 mg, 1.25 mmol, 5 mol %), sodium hydroxide (6.0 g, 150 mmol), 4-methoxybenzyl chloride (4.7 g, 30 mmol), water (6 ml) and trans-1-2-dichioroethane (20 ml) was stirred vigorously under reflux until tlc (10% acetone/hexane) showed the reaction to be complete (typically 3–7 hours). On completion the reaction mixture was cooled and diluted with water (20 ml) and methylene chloride (20 ml). The organic layer was separated and washed with water until the washings were neutral (4×30 ml). The organic layer was dried (MgSO$_4$) and concentrated to dryness. Purification by flash chromatography (8% acetone/hexane) yielded the fully protected glycerol as a colourless oil.

(ii) A mixture of the fully protected glycerol (vide supra) (1.0 g), hydrochloric acid (1M, 10 ml) and methanol (15 ml) were stirred together at room temperature for 1 hour. (At this point the analysis (25% ethyl acetate/hexane) showed complete disappearance of the starting material and the formation of one new spot corresponding to the product). The bulk of the solvent was removed, brine (20 ml) was added and the product was extracted into methylene chloride (4×30 ml). The combined extracts were dried (MgSO$_4$) and concentrated to dryness. On standing under high vacuum the product crystallised. On one occasion it was purified by flash chromatography (3% methanol/methylene chloride) although this was not generally necessary. This monoprotected glycerol was the starting point for attachment of the fatty acids.

(iii) A solution of DCC (1.1 g, 5.3 mmol) and DMAP (0.67 g, 5.3 mmol) in methylene chloride (10 ml) was added to a solution of the monoprotected glycerol (1.0 g, 4.7 mmol) and GLA (98%, 1.24 g, 4.4 mmol) in methylene chloride (40 ml) at 0° C. under nitrogen. The reaction was stirred overnight, warming up to room temperature. As the reaction proceeded a precipitate of dicyclohexylurea formed. Hexane (60 ml) was added to precipitate more dicyclohexylures and the reaction was filtered and concentrated to dryness. Careful purification by flash chromatography (20% ethyl acetate/hexane) yielded the monoprotected 1-monoacylglycerol as a colourless oil. By tic it was clear that it was not contaminated by any of the monoprotected 2-monoacylglycerol isomer.

(iv) A solution of DCC (0.72 g, 3.45 mmol) and DMAP (0.36 g, 2.92 mmol) in methylene chloride (10 ml) was added to a solution of the monoprotected 1-monoacylglycerol (1.25 g, 2.65 mmol) and CA (99%, 0.83 g, 2.92 mmol) in methylene chloride (40 ml) at room temperature under nitrogen. The reaction was stirred overnight. As the reaction proceeded a precipitate of dicyclohexylurea formed. Hexane (60 ml) was added to precipitate more dicyclohexylurea and the reaction was filtered and concentrated to dryness. Purification by flash chromatography (8% ethyl acetate/hexane) yielded the monoprotected diacylglycerol as a colourless oil.

(v) Bromodimethylborane (220 µl, 2.2 mmol) was added by syringe to a solution of the monoprotected diacylglycerol (800 mg, 1.1 mmol) in methylene chloride (20 ml) at −78° C. (external cooling by dry ice/acetone) under nitrogen. After 3 minutes at −78° C. the reaction was quenched by the addition of diethyl ether (200 ml). Tlc analysis (4% acetone/chloroform) indicated that the reaction had gone substantially towards completion. The mixture was washed with water (5×100 ml), brine (100 ml), dried (MgSO$_4$) and concentrated to dryness. The product was used directly in the next step without any further purification.

(vi) A solution of the diacylglycerol (1.1 mmol) and triethylamine (210 µl, 1.5 mmol) was cooled to 0° C. To this was added a solution of 2-chloro-1,3,2-dioxaphospholane-2-oxide (180 mg, 1.25 mmol) in toluene (5 ml). After 6 hours a further portion of the chlorophosphidate (150 mg) was added and the mixture was stirred overnight, warming up to room temperature. Tlc analysis (20% ethyl acetate/toluene) showed almost complete disappearance of starting material and the formation of a new compound. The solvents were removed under reduced pressure and, after drying under vacuum at 45° C. for several hours, the product was used directly in the next stage of the reaction.

(vii) A solution of trimethylamine in anhydrous acetonitrile (16 g gas in 100 ml) was prepared. The crude product from the previous step was dissolved in this solution (4 ml) and transferred to a sealed tube. The tube was purged with nitrogen and heated at 65° C. for 48 hours. The reaction was cooled. The mixture was two layers. The bottom layer was the phosphatidylcholine and the top layer solvent. The mixture was dissolved in chloroform, transferred to a round bottomed flask and concentrated to dryness. Purification by flash chromatography (chloroform: methanol: water 65:25:4) yielded the pure mixed acid phosphatidylcholine as a yellow waxy solid. Tlc analysis (chloroform: methanol: water 65:25:4) showed only one clean spot. A sample of the phospholipid was transmethylated and the fatty acid methyl esters determined by g.c.

Synthesis of
1,2-di(z-z-z-6,9,12-octadecatrienoyl)-gn-glycerol-3-phosphocoline

A mixture of crystalline L-α-glycerophoshorylcholine-cadmium chloride complex (from Sigma) (490 mg; 1.1 mmol) (dried by evaporation from ethanol) (2×30 ml) and toluene (4×30 ml), GLA acid chloride (890 mg; 3 mmol) and 4-N,N-dimethylaminopyridine (370 mg; 3 mmol) in methylene chloride (20 ml) was stirred overnight under nitrogen at room temperature. Initially the reaction mixture was a dense suspension but after the overnight period it was an almost clear solution. Tlc analysis in two systems (1. chloroform/methanol/water: 65/25/4; 2. chloroform/methanol/ammonium hydroxide: 65/30/5) showed the presence of two new compounds. The major component had an R$_f$ value consistent with the desired product and the minor component was thought to be the corresponding lysophospharycholine. The reaction mixture was concentrated to dryness and suspended in methanol/chloroform/water: 5/4/1 (20 ml).

A dense white precipitate formed. The mixture was applied to a mixed resin ion exchange column (approximately 25 ml each of Dowex 50×4-100 (H$^+$form) and Dowex 1×2-100 (HO$^-$form)). (This was to remove both the DMAP and the cadmium chloride). The phospholipid was eluted with methanol/chloroform/water: 5/4/1 (200 ml) and the eluent was concentrated to dryness. Ethanol and toluene were added to aid complete removal of water. A solution of the crude mixture in methylene chloride was applied to a column of silica gel (20 ml) which had previously been packed in methylene chloride. GLA was eluted with methylene chloride (250 ml) and the product was then eluted with methanol/chloroform/water: 5/4/1. Fractions containing the pure product were pooled and concentrated. The residue was dissolved in methylene chloride, dried (magnesium sulfate), concentrated and finally dried under high vacuum. The product was a waxy solid which was homogenous by tlc analysis. At this stage no further analysis has been carried out. Yield=310 mg (36%).

An analogous procedure has been carried out using GLA acid anhydride rather than GLA acid chloride. This gave a much better yield (72% with a 48 hour reaction period). However, this sample has not been used for testing.

We claim:

1. A phospholipid comprising two different unsaturated fatty acids, the fatty acids being linked to the glycerol backbone at the 1- and 2-positions and selected from the twelve n-6 and n-3 essential fatty acids, oleic acid, parinaric acid and columbinic acid, the two fatty acids linked together with a phospholipid selected from the group consisting of serine, choline, ethanolamine and inositol.

2. A phospholipid according to claim 1, wherein the fatty acids are selected from the group consisting of GLA, DGLA, AA, EPA and DHA.

3. A phospholipid according to claim 1, wherein the fatty acids are in a combination selected from the group consisting of GLA or DGLA with AA, EPA or DHA; AA with EPA or DHA; and EPA with DHA.

4. A therapeutic, nutritional or cosmetic phospholipid composition comprising two different unsaturated fatty acids, the fatty acids being linked at the glycerol backbone at the 1- and 2-positions and selected from the twelve n-6 and n-3 essential fatty acids, oleic acid, parinaric and columbinic acid, the two fatty acids linked together to form a single molecule with a phospholipid selected from the group consisting of serine, choline, ethanolamine and inositol.

5. The phospholipid composition according to claim 4, wherein the fatty acids are selected from the group consisting of GLA, DGLA, AA, EPA and DHA.

6. The phospholipid composition according to claim 4, wherein the fatty acids are in a combination selected from the group consisting of GLA or DGLA with AA, EPA or DHA; AA with EPA or DHA; and EPA with DHA.

7. The phospholipid composition according to claim 4, in which said phosphilipid forms, by weight, at least 20% of the total phospholipid present.

8. The phospholipid composition of claim 7, in which said phospholipid forms, by weight, more than 40% of the total phospholipid present.

9. The phospholipid composition of claim 8, in which said phospholipid forms, by weight, more than 70% of the total phospholipid present.

10. The phospholipid composition of claim 9, in which said phospholipid forms, by weight, more than 90% of the total phospholipid present.

11. The phospholipid composition of claim 4, in the form of a pharmaceutical or dietary composition suited to the administration of 1 mg to 100 g said phospholipid daily.

12. The phospholipid composition according to claim 11, in the form of a pharmaceutical or dietary composition suited to the administration of 100 mg to 20 g said phospholipid daily.

13. The phospholipid composition according to claim 12, in the form of a pharmaceutical or dietary composition suited to the administration of 500 mg to 4 g said phospholipid daily.

14. The phospholipid composition according to claim 4, comprising by weight 0.01 to 60% of said phospholipid.

15. The phospholipid composition according to claim 14, comprising by weight 0.2 to 30% of said phospholipid.

16. The phospholipid composition according to claim 15, comprising by weight 1 to 20% of said phospholipid.

* * * * *